(12) United States Patent
Luo

(10) Patent No.: US 6,672,095 B1
(45) Date of Patent: Jan. 6, 2004

(54) THERAPEUTIC FREEZING DEVICE AND METHOD

(76) Inventor: Chin-Kuang Luo, 5F, No. 56, Min-Chuan Rd., Chung Dist., Taichung City (TW)

( * ) Notice: Subject to any disclaimer, the term of this patent is extended or adjusted under 35 U.S.C. 154(b) by 0 days.

(21) Appl. No.: 10/306,496

(22) Filed: Nov. 27, 2002

(30) Foreign Application Priority Data

Jun. 28, 2002 (TW) ........................ 91114370 A

(51) Int. Cl.[7] ................ F25D 3/00; A61B 18/18; A61F 7/00; A61F 7/12
(52) U.S. Cl. ................ 62/293; 62/259.3; 607/96; 606/23
(58) Field of Search ................ 62/51.1, 293, 259.3; 607/96; 606/23

(56) References Cited

U.S. PATENT DOCUMENTS

| | | | | |
|---|---|---|---|---|
| 5,078,958 A | * | 1/1992 | Danko et al. ................ 376/272 |
| 6,039,730 A | * | 3/2000 | Rabin et al. .................. 606/23 |
| 6,132,823 A | * | 10/2000 | Qu ............................ 428/34.6 |
| 6,527,765 B2 | * | 3/2003 | Kelman et al. ............... 606/22 |
| 2002/0087152 A1 | * | 7/2002 | Mikus et al. ................. 606/21 |
| 2002/0182332 A1 | * | 12/2002 | Qu ........................... 427/419.1 |

* cited by examiner

Primary Examiner—William C. Doerrler
(74) Attorney, Agent, or Firm—Trop, Pruner & Hu, P.C.

(57) ABSTRACT

A therapeutic freezing device includes a barrel and a superconducting needle. The barrel defines a receiving space adapted to receive a coolant medium. The superconducting needle is mounted on the barrel and is adapted to contact the coolant medium so that the low-temperature of the coolant medium is transferred to the superconducting layer. The superconducting needle includes a superconductive material.

8 Claims, 3 Drawing Sheets

THERAPEUTIC FREEZING DEVICE AND METHOD

CROSS-REFERENCE TO RELATED APPLICATION

This application claims priority of Taiwanese application No. 091114370, filed on Jun. 28, 2002.

BACKGROUND OF THE INVENTION

1. Field of the Invention

The invention relates to a therapeutic freezing device, more particularly to a therapeutic freezing device to be used in combination with a coolant medium and insertable into an abnormal tissue of a patient to freeze and destroy the tissue. The invention also relates to a therapeutic freezing method which utilizes the therapeutic freezing device.

2. Description of the Related Art

Conventional freezing therapy involves the destruction of abnormal tissue, such as cancerous tissue, by ultra-low temperature coolant medium. To conduct freezing therapy, a probe device is inserted into a target site of an abnormal tissue of a patient, and liquefied nitrogen is then injected into the target site of the abnormal tissue through the probe device so as to destroy the abnormal tissue.

However, use of the conventional probe device results in the following shortcomings:

1. When the liquefied nitrogen flows from a top end of the probe device to a needle end of the probe device through a main body of the probe device, an extremely low temperature of about −200° C. resulting from the liquefied nitrogen may also destroy normal tissue in contact with the main body of the probe device.
2. Since the liquefied nitrogen is directly injected toward the tissue of the patient in the conventional probe device, the residual nitrogen in the tissue can result in adverse side effects for the patient.

SUMMARY OF THE INVENTION

Therefore, the object of the present invention is to provide a therapeutic freezing device to be used in combination with a coolant medium so as to transfer the low-temperature of the coolant medium to the abnormal tissue that is to be treated through a superconducting layer.

According to one aspect of the present invention, a therapeutic freezing device is provided to include a barrel and a superconducting needle. The barrel defines a receiving space adapted to receive the coolant medium and having a coolant medium entrance end. The superconducting needle is mounted on the barrel and is adapted to contact the coolant medium so that the low-temperature of the coolant medium is transferred to the superconducting needle. The superconducting needle includes a superconductive material.

According to another aspect of the present invention, a therapeutic freezing method is provided to include the steps of:

inserting a superconducting needle into a target site of an abnormal tissue of a patient;
detecting and observing depth to which the superconducting needle must be inserted, and guiding the superconducting needle to reach said depth;
contacting a coolant medium with the superconducting needle to lower the temperature of the superconducting needle; and
contacting the superconducting needle with the tissue to freeze and destroy the tissue without contact between the coolant medium and the tissue.

In a further another aspect of this invention, a superconducting needle is provided for use in the inventive therapeutic freezing device.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENT

Figure 1:
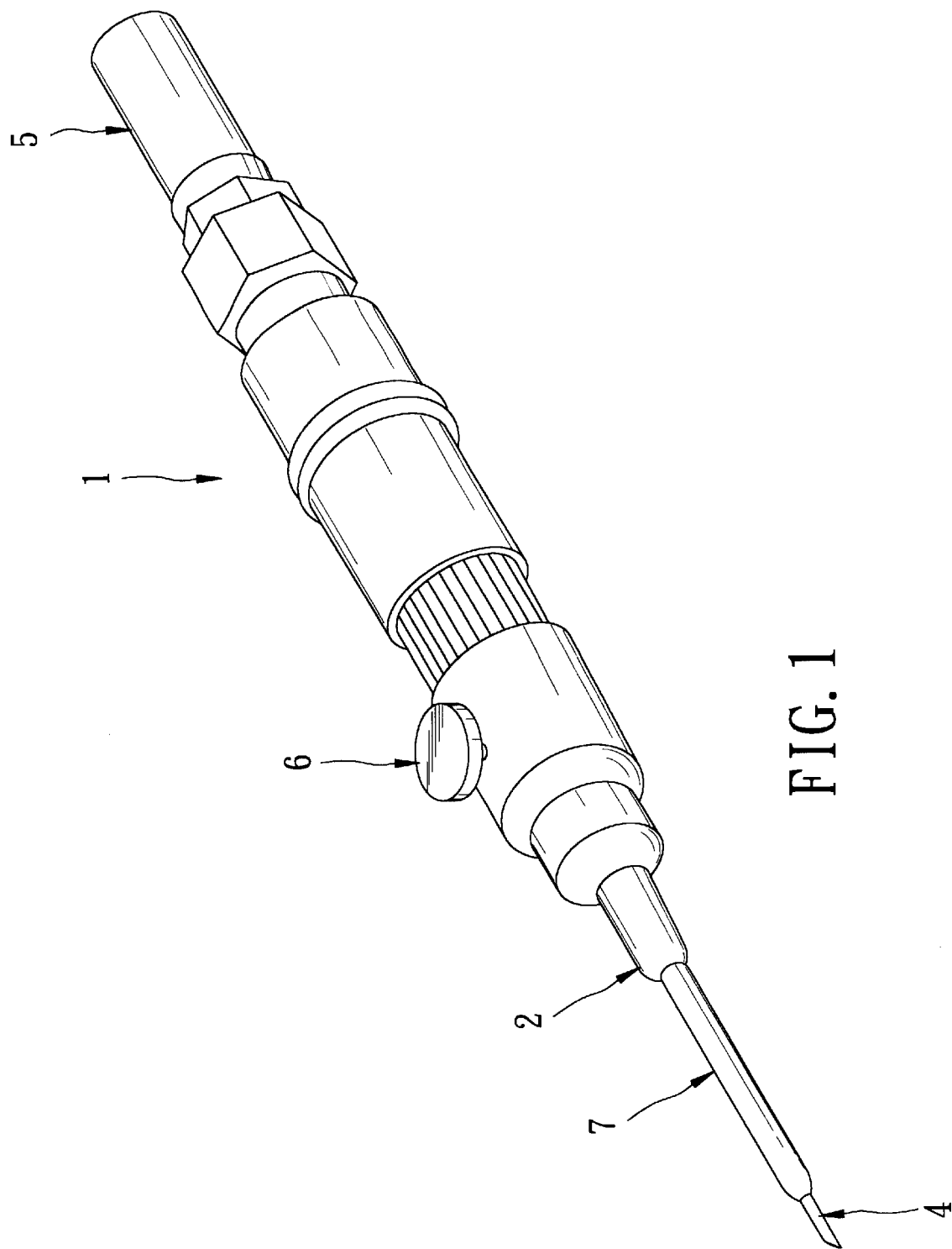
FIG. 1 is a perspective view of the first preferred embodiment of a therapeutic freezing device according to this invention.
Figure 2:
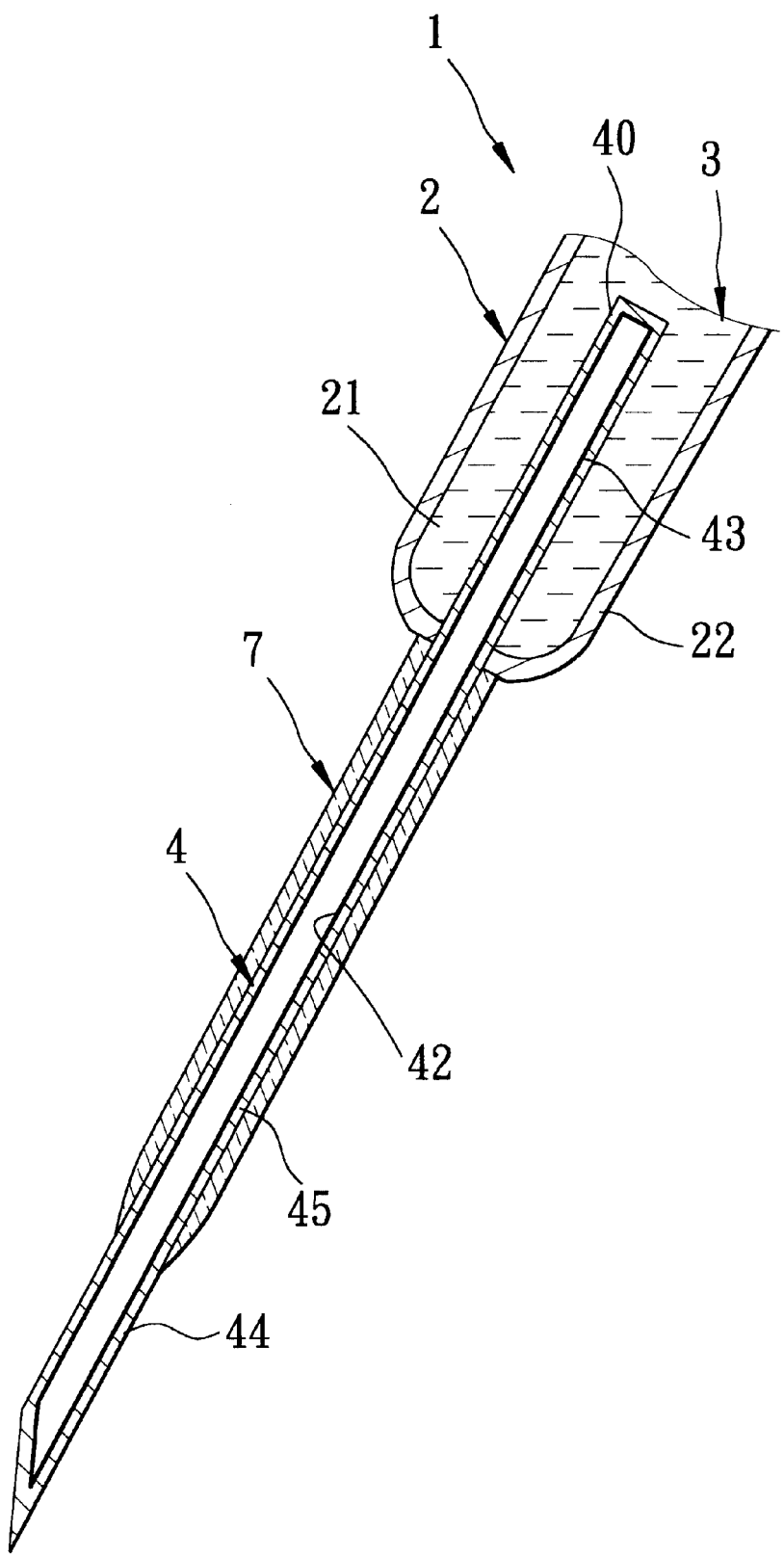
FIG. 2 is a sectional view of the first preferred embodiment.

Referring to FIGS. 1 and 2, the first preferred embodiment of a therapeutic freezing device 1 according to this invention is shown to include a barrel 2, a superconducting needle 4, a transporting tube 5 detachably connected to the barrel 2 for transporting a coolant medium 3 into the barrel 2, and a control valve 6 mounted on the barrel 2 for controlling the flow rate of the coolant medium 3 flowing into the barrel 2.

The barrel 2 defines a receiving space 21 adapted to receive the coolant medium 3 and having a coolant medium entrance end (not shown in the figures). Liquefied nitrogen is used as the coolant medium 3 in this preferred embodiment. The superconducting needle 4 is mounted on the barrel 2 and is adapted to contact the coolant medium 3 so that the low-temperature of the coolant medium 3 is transferred to the superconducing needle 4. The superconducting needle 4 includes a hollow body 40 and a superconducting layer 42 made of a superconductive material, disposed in the hollow body 40, and forming a superconductor lining on an inner wall surface of the hollow body 40. The superconducting needle 4 has a contacting end portion 43 mounted in the receiving space 21 of the barrel 2 adjacent to an end 22 of the barrel 2 away from the coolant medium entrance end so as to contact the coolant medium 21 in the barrel 2 for thermal exchange, and a freezing end 44 extending away from the contacting end portion 43 so that the low-temperature of the coolant medium 21 is transferred from the contacting end portion 43 to the freezing end 44 through the superconductor lining on the inner wall surface of the hollow body 40 of the superconducting needle 4.

The superconducting needle 4 further includes an insulated middle portion 45 between the contacting end portion 43 and the freezing end 44. The insulated middle portion 45 of the superconducting needle 4 extends out of the barrel 2 and includes an insulating shell 7 covering the insulated middle portion 45. The freezing end 44 of the superconducting needle 4 extends out of the insulating shell 7. The insulating shell 7 is made of any suitable material, such as reinforced glass or any other suitable rigid material.

The hollow body 40 of the superconducting needle 4 is made of a heat conductive material, such as aluminum, copper, or a metal alloy, or a material which exhibits excellent heat conducting characteristics.

The superconducting layer 42 is formed by a vacuum deposition process. In actual practice, the inner surface of the hollow body 40 is passivated, washed and dried. The superconductive material is then injected or filled into the hollow body 40, which is then vacuumed and sealed so as to form the superconductor lining on the inner surface of the hollow body 40.

It is noted that the thermal superconductive material includes at least one compound selected from the group consisting of sodium peroxide, sodium oxide, beryllium oxide, manganese sesquioxide, aluminum dichromate, calcium dichromate, boron oxide, dichromate radical, and combinations thereof; at least one compound selected from the group consisting of cobaltous oxide, manganese sesquioxide, beryllium oxide, strontium chromate, strontium carbonate, rhodium oxide, cupric oxide, β-titanium, potassium dichromate, boron oxide, calcium dichromate, manganese dichromate, aluminum dichromate, dichromate radical, and combinations thereof; and at least one compound selected from the group consisting of denatured rhodium oxide, potassium dichromate, denatured radium oxide, sodium dichromate, silver dichromate, monocrystalline silicon, beryllium oxide, strontium chromate, boron oxide, sodium peroxide, β-titanium, a metal dichromate, and combinations thereof.

Figure 3:
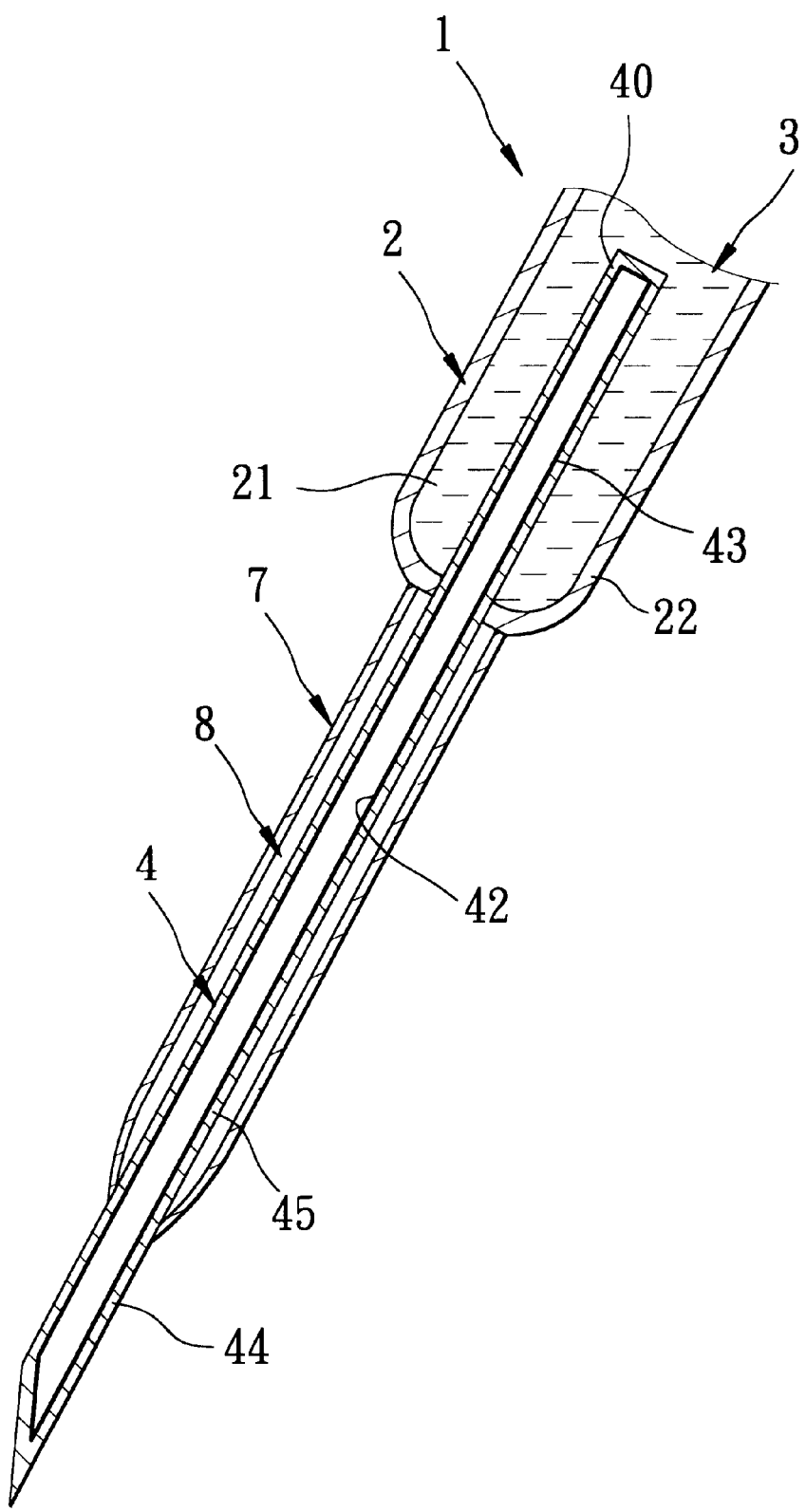
FIG. 3 is a sectional view of the second preferred embodiment of a therapeutic freezing device according to this invention.

Referring to FIG. 3, the second preferred embodiment of a therapeutic freezing device according to this invention is shown to be similar to the first preferred embodiment, except the insulating shell 7 is spaced from the insulated middle portion 45 of the superconducting needle 4 so as to define a vacuum space 8 therebetween.

In use, the superconducting needle 4 of the therapeutic freezing device 1 is inserted into a target site of an abnormal tissue of a patient. An ultrasonic detector is used to determine the inserting depth of the superconducting needle 4. The liquefied nitrogen is then injected into the receiving space 21 of the barrel 2 through the transporting tube 5. The low-temperature of the liquefied nitrogen is thermally exchanged from the liquefied nitrogen to the contacting end portion 43 of the superconducting needle 4, and is then transferred from the contacting end portion 43 to the freezing end 44 through the superconductor lining on the inner wall surface of the hollow body 40 of the superconducting needle 4 so as to freeze and destroy the abnormal tissue without contact between the coolant medium and the tissue.

Moreover, since the insulated middle portion 45 of the superconducting needle 4 is covered with the insulating shell 7, normal tissue will not be destroyed during the freezing therapeutic treatment. Additionally, as shown in FIG. 3, when the vacuum space 8 is formed between the insulating shell 7 and the insulated middle portion 45 of the superconducting needle 4, the insulating effect for preventing destruction of normal tissue during the freezing therapeutic treatment can be further enhanced.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A therapeutic freezing device to be used in combination with a coolant medium and insertable into an abnormal tissue of a patient to freeze and destroy the tissue, comprising:

a barrel defining a receiving space adapted to receive the coolant medium; and a superconducting needle mounted on said barrel, wherein said superconducting needle includes a hollow body and a superconducting layer made of a superconductive material, disposed in said hollow body and forming a superconductor lining on an inner wall surface of said hollow body, said superconducting needle having a contacting end portion received within said receiving space of said barrel, and a freezing end extending out of said barrel, said contacting end portion and said freezing end being sealed fluidly so that no coolant medium enters into said hollow body.

2. The therapeutic freezing device as claimed in claim 1, wherein said superconducting needle further includes an insulated middle portion between said contacting end portion and said freezing end.

3. The therapeutic freezing device as claimed in claim 2, wherein said insulated middle portion of said superconducting needle extends out of said barrel and includes an insulating shell covering said insulated middle portion, said freezing end extending out of said shell.

4. The therapeutic freezing device as claimed in claim 3, wherein said insulating shell is spaced from said insulated middle portion so as to define a vacuum space therebetween.

5. The therapeutic freezing device as claimed in claim 1, wherein the coolant medium is liquefied nitrogen.

6. The therapeutic freezing device as claimed in claim 1, wherein said hollow body of said superconducting needle is made of a conductive metal selected from a group consisting of copper and aluminum.

7. The therapeutic freezing device as claimed in claim 6, wherein said superconductive material is introduced into said hollow body, and said superconducting lining is formed by a vacuum deposition process.

8. The therapeutic freezing device as claimed in claim 1, wherein said hollow body is vacuumed.

* * * * *